United States Patent
Li et al.

(10) Patent No.: US 10,722,182 B2
(45) Date of Patent: Jul. 28, 2020

(54) METHOD AND APPARATUS FOR HEART RATE AND RESPIRATION RATE ESTIMATION USING LOW POWER SENSOR

(71) Applicant: Samsung Electronics Co., Ltd., Suwon-si (KR)

(72) Inventors: Yelei Li, Santa Clara, CA (US); Matthew C. Wiggins, San Jose, CA (US)

(73) Assignee: Samsung Electronics Co., Ltd. (KR)

(*) Notice: Subject to any disclaimer, the term of this patent is extended or adjusted under 35 U.S.C. 154(b) by 616 days.

(21) Appl. No.: 15/168,531

(22) Filed: May 31, 2016

(65) Prior Publication Data
US 2017/0273635 A1 Sep. 28, 2017

Related U.S. Application Data

(60) Provisional application No. 62/313,910, filed on Mar. 28, 2016.

(51) Int. Cl.
*A61B 5/02* (2006.01)
*A61B 5/00* (2006.01)
(Continued)

(52) U.S. Cl.
CPC .......... *A61B 5/7278* (2013.01); *A61B 5/0015* (2013.01); *A61B 5/02055* (2013.01);
(Continued)

(58) Field of Classification Search
CPC ..... A61B 5/7278; A61B 5/7207; A61B 5/113; A61B 5/681; A61B 5/7282; A61B 5/7225;
(Continued)

(56) References Cited

U.S. PATENT DOCUMENTS 6,421,558 B1 * 7/2002 Huey .................. A61B 5/04882
600/546
7,035,679 B2 4/2006 Addison et al.
(Continued)

FOREIGN PATENT DOCUMENTS

| CN | 104424488 A | 3/2015 |
|---|---|---|
| EP | 1166715 A2 | 1/2002 |
| EP | 1166715 A3 | 4/2003 |

OTHER PUBLICATIONS

MEMS Accelerometer Based Heart & Respiration Rate Detection Module, http://www.murata.com/~/media/webrenewal/campaign/ads/europe/healthcare/bcg_flyer_0901.ashx?la=en-g.
(Continued)

*Primary Examiner* — Navin Natnithithadha
*Assistant Examiner* — Andrey Shostak
(74) *Attorney, Agent, or Firm* — McAndrews, Held & Malloy, Ltd.

(57) ABSTRACT

Provided is a system for measuring biological signals of a user, which includes a sensor module configured to acquire ballistocardiogram (BCG) signals of a user via a present channel, where the present channel is at least one channel of the sensor module, a decomposition module configured to decompose the BCG signals to decomposed signals, a reconstruction module configured to reconstruct at least a portion of the decomposed signals to reconstructed signals, a processing module configured to process the reconstructed signals to at least one of a heart rate, respiration rate, phases of respiration, and blood pressure, and a display module configured to display at least one output corresponding to the at least one of the heart rate, the respiration rate, phases of respiration, and the blood pressure on a display device.

18 Claims, 13 Drawing Sheets

(51) Int. Cl.
  *A61B 5/11* (2006.01)
  *A61B 5/0205* (2006.01)
  *A61B 5/113* (2006.01)
  *A61B 5/024* (2006.01)

(52) U.S. Cl.
  CPC ............ *A61B 5/1102* (2013.01); *A61B 5/113* (2013.01); *A61B 5/681* (2013.01); *A61B 5/726* (2013.01); *A61B 5/7207* (2013.01); *A61B 5/7225* (2013.01); *A61B 5/7282* (2013.01); *A61B 5/742* (2013.01); *A61B 5/02416* (2013.01); *A61B 2562/0219* (2013.01); *A61B 2562/04* (2013.01)

(58) Field of Classification Search
  CPC ..... A61B 5/0015; A61B 5/1102; A61B 5/726; A61B 5/742; A61B 5/02055; A61B 5/02416; A61B 2562/04; A61B 2562/0219
  See application file for complete search history.

(56) References Cited

U.S. PATENT DOCUMENTS

| | | | |
|---|---|---|---|
| 2011/0066042 A1* | 3/2011 | Pandia | A61B 5/029 600/484 |
| 2012/0184862 A1 | 7/2012 | Foo et al. | |
| 2013/0109989 A1 | 5/2013 | Busse et al. | |
| 2013/0310979 A1* | 11/2013 | Herr | B62D 57/032 700/258 |
| 2014/0005988 A1* | 1/2014 | Brockway | H03H 17/0248 703/2 |
| 2014/0121554 A1* | 5/2014 | Sarma | A61B 5/7267 600/544 |
| 2014/0213858 A1 | 7/2014 | Presura et al. | |
| 2014/0288875 A1 | 9/2014 | Donaldson | |
| 2015/0112209 A1 | 4/2015 | Blaber et al. | |
| 2015/0157239 A1 | 6/2015 | Rissacher et al. | |
| 2015/0305632 A1 | 10/2015 | Najarian et al. | |
| 2016/0007935 A1 | 1/2016 | Hernandez et al. | |
| 2016/0081563 A1 | 3/2016 | Wiard et al. | |
| 2016/0089086 A1* | 3/2016 | Lin | A61B 5/02438 600/479 |
| 2016/0213934 A1* | 7/2016 | Shen | A61N 1/36542 |
| 2018/0279961 A1* | 10/2018 | Zhu | A61B 5/1102 |

OTHER PUBLICATIONS

Jin, Jingjing, et al., "A Novel Heart Rate Detection Algorithm in Ballistocardiogram Based on Wavelet Transform" © 2009 IEEE, pp. 76-79.

Phan, D.H. et al., "Estimation of respiratory waveform and heart rate using an accelerometer" 30th Annual International IEEE EMBS Conference Vancouver, British Columbia, Canada, Aug. 20-24, 2008, pp. 4916-4919.

Hoff, L. et al., "Measurements of Heart Motion using Accelerometers" Proceedings of the 26th Annual International Conference of the IEEE EMBS San Francisco, CA, USA—Sep. 1-5, 2004, 2049-2051.

Gilaberte, S. et al., Heart and Respiratory Rate Detection on a Bathroom Scale Based on the Ballistocardiogram and the Continuous Wavelet Transform, 32nd Annual International Conference of the IEEE EMBS Buenos Aires, Argentina, Aug. 31-Sep. 4, 2010, pp. 2557-2560.

Extended European Search Report Appln No. EP 17159081 dated Jan. 17, 2018 (14 pages).

* cited by examiner

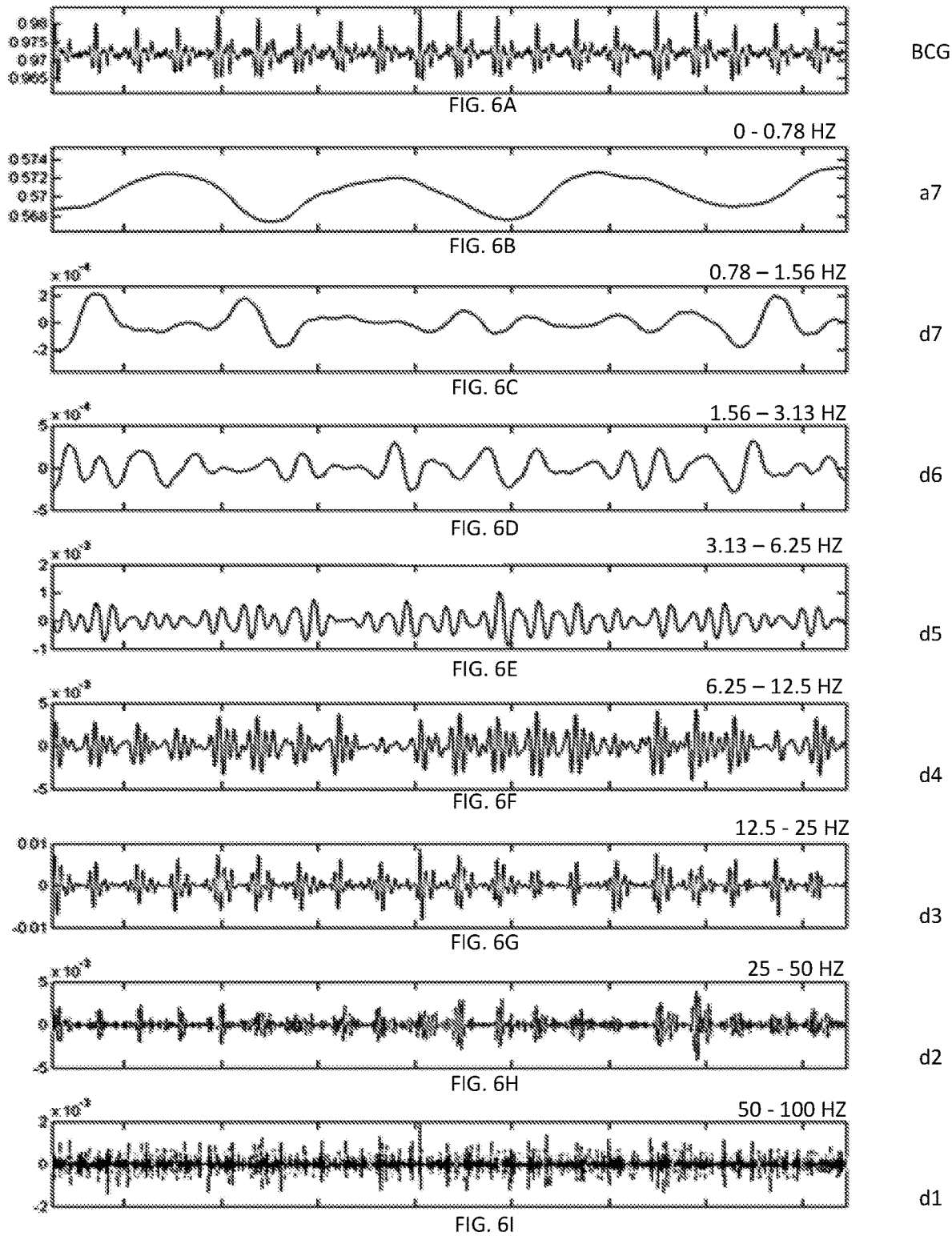
FIG. 6A — BCG
FIG. 6B — 0 - 0.78 HZ — a7
FIG. 6C — 0.78 – 1.56 HZ — d7
FIG. 6D — 1.56 – 3.13 HZ — d6
FIG. 6E — 3.13 – 6.25 HZ — d5
FIG. 6F — 6.25 – 12.5 HZ — d4
FIG. 6G — 12.5 - 25 HZ — d3
FIG. 6H — 25 - 50 HZ — d2
FIG. 6I — 50 - 100 HZ — d1

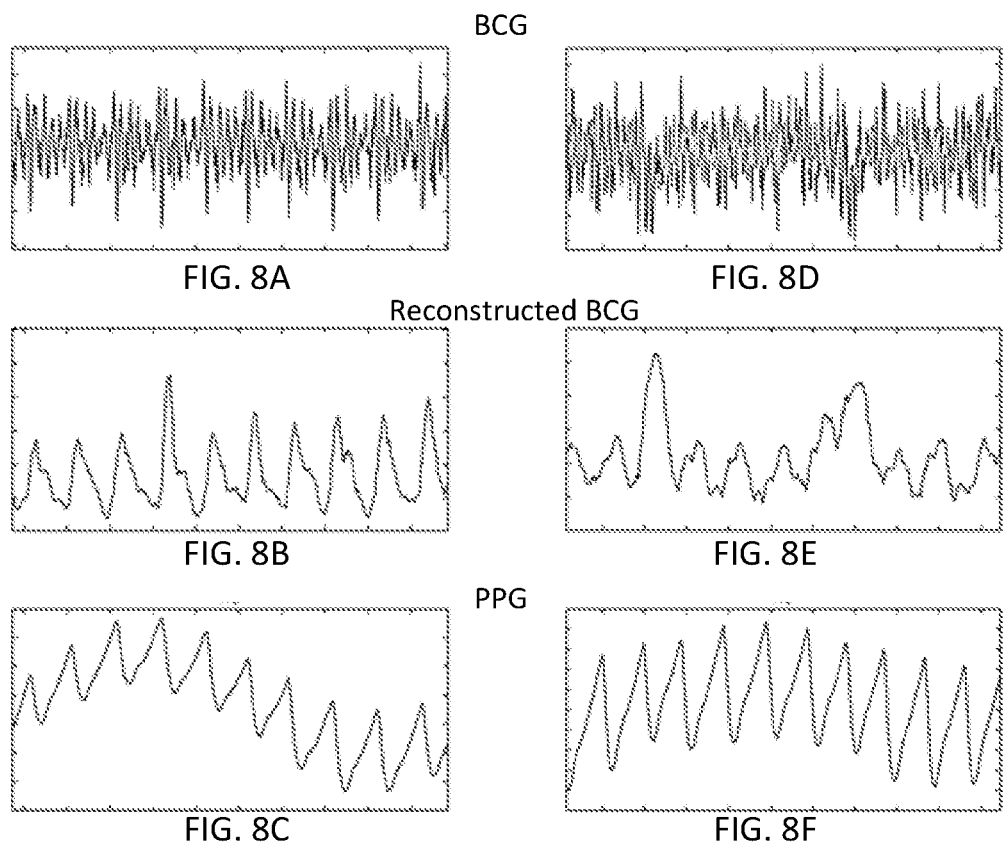

METHOD AND APPARATUS FOR HEART RATE AND RESPIRATION RATE ESTIMATION USING LOW POWER SENSOR

RELATED APPLICATION(S)

This application claims the benefit of the U.S. Provisional Application 62/313,910, filed on Mar. 28, 2016, the disclosure of which is incorporated herein in its entirety by reference. The U.S. application Ser. No. 14/924,565 is incorporated in its entirety by reference.

BACKGROUND

The present disclosure relates to measuring a user's body signals, and more particularly, to a method and apparatus for heart rate and respiration rate estimation using low power sensor.

As with any portable electronic device, it is desirable for a wearable sensor device that monitors biosignals to have a long battery life. Typically, longer battery life can be provided for a wearable device by providing less information content. However, in some cases the reduced information content may not be acceptable.

A photoplethysmogram (PPG) sensor device typically determines and estimates heart rate and respiration rate based on a PPG based heart rate method. However, a PPG sensor consumes a lot of power.

SUMMARY

Provided are method and apparatus for continuous triage and subsequent escalation based on undesired biosignals or biometrics. An exemplary embodiment may include a non-transitory machine-readable medium storing machine executable instructions that when executed causes a computing system to control operations for measuring biological signals of a user. The operations may include acquiring ballistocardiogram (BCG) signals of a user via a present channel, wherein the present channel is at least one channel of a sensor. The BCG signals may be processed to decomposed signals, and the decomposed signals may be processed to reconstructed signals. The reconstructed signals may then be processed to at least one of a heart rate, respiration rate, phases of respiration, and blood pressure, which may be displayed for viewing by the user or others.

Another exemplary embodiment may be a system for measuring biological signals of a user, comprising a sensor module configured to acquire ballistocardiogram (BCG) signals of a user via a present channel, wherein the present channel is at least one channel of the sensor module. The system may also include a decomposition module configured to decompose the BCG signals to decomposed signals and a reconstruction module configured to reconstruct at least a portion of the decomposed signals to reconstructed signals. A processing module may be configured to process the reconstructed signals to at least one of a heart rate, respiration rate, phases of respiration and blood pressure. One or more of the heart rate, respiration rate, phases of respiration and blood pressure may be displayed on a display module for viewing by the user or others.

Another exemplary embodiment may be a method for measuring biological signals of a user, comprising acquiring ballistocardiogram (BCG) signals of a user via a present channel, wherein the present channel is at least one channel of a sensor. The BCG signals may be decomposed to decomposed signals, and at least a portion of the decomposed signals may be reconstructed to reconstructed signals. The reconstructed signals may be processed to at least one of a heart rate, respiration rate, phases of respiration, and blood pressure, and one or more of the heart rate, the respiration rate, the phases of respiration, and/or the blood pressure may be displayed on a display device.

Additional aspects will be set forth in the description that follows and/or learned by practice of the presented exemplary embodiments.

BRIEF DESCRIPTION OF THE DRAWINGS

These and/or other aspects will become apparent and more readily appreciated from the following description of the exemplary embodiments, taken in conjunction with the accompanying drawings.

FIG. 6A illustrates an exemplary BCG signal in accordance with an embodiment of the present disclosure.

FIG. 6B illustrates wavelet-based BCG decomposition waveforms in the frequency range of 0 to 0.78 Hz in accordance with an embodiment of the present disclosure.

FIG. 6C illustrates wavelet-based BCG decomposition waveforms in the frequency range of 0.78 to 1.56 Hz in accordance with an embodiment of the present disclosure.

FIG. 6D illustrates wavelet-based BCG decomposition waveforms in the frequency range of 1.56 to 3.13 Hz in accordance with an embodiment of the present disclosure.

FIG. 6E illustrates wavelet-based BCG decomposition waveforms in the frequency range of 3.13 to 6.25 Hz in accordance with an embodiment of the present disclosure.

FIG. 6F illustrates wavelet-based BCG decomposition waveforms in the frequency range of 6.25 to 12.5 Hz in accordance with an embodiment of the present disclosure.

FIG. 6G illustrates wavelet-based BCG decomposition waveforms in the frequency range of 12.5 to 25 Hz in accordance with an embodiment of the present disclosure.

FIG. 6H illustrates wavelet-based BCG decomposition waveforms in the frequency range of 25 to 50 Hz in accordance with an embodiment of the present disclosure.

FIG. 6I illustrates wavelet-based BCG decomposition waveforms in the frequency range of 50 to 100 Hz in accordance with an embodiment of the present disclosure.

FIG. 8A illustrates exemplary BCG waveforms in accordance with an embodiment of the present disclosure.

FIG. 8B illustrates exemplary waveforms of reconstructed BCG signals in accordance with an embodiment of the present disclosure.

FIG. 8C illustrates exemplary PPG waveforms in accordance with an embodiment of the present disclosure.

FIG. 8D illustrates exemplary BCG waveforms in accordance with an embodiment of the present disclosure.

FIG. 8E illustrates exemplary waveforms of reconstructed BCG signals in accordance with an embodiment of the present disclosure.

FIG. 8F illustrates exemplary PPG waveforms in accordance with an embodiment of the present disclosure.

DETAILED DESCRIPTION

Figure 1:
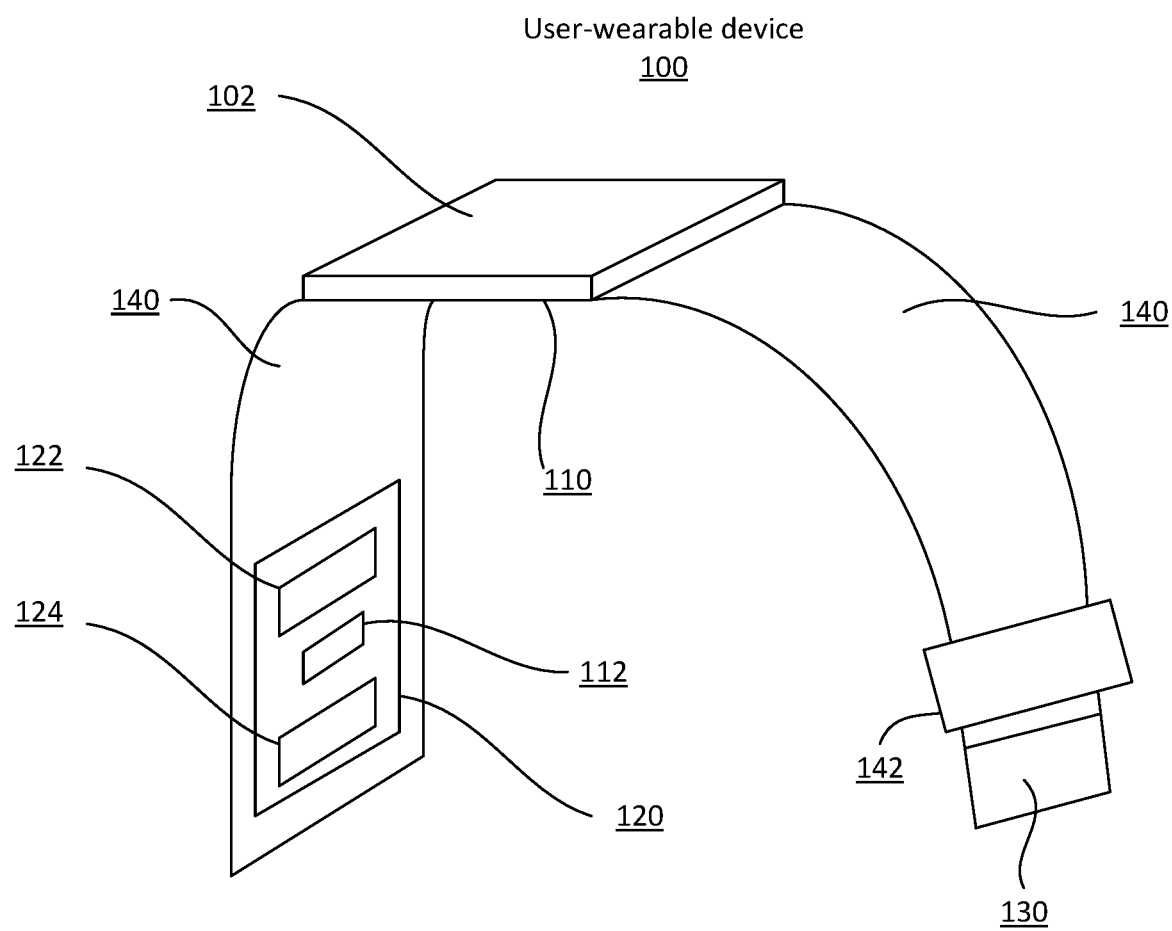
FIG. 1 is a diagram illustrating an electronic device in accordance with an embodiment of the present disclosure.

Advantages and features of one or more embodiments of the present disclosure may be understood more readily by reference to the following detailed description of the embodiments and the accompanying drawings.

In this regard, the present embodiments should not be construed as being limited to the descriptions set forth herein. Rather, these embodiments are provided as examples so that this disclosure will be thorough and complete and will fully convey the concept of the present embodiments to one of ordinary skill in the art. The appended claims illustrate some of the embodiments of the present disclosure.

Like reference numerals refer to like elements throughout the specification. All terms including descriptive or technical terms used herein should be construed as having meanings that are obvious to one of ordinary skill in the art. When a term has an ambiguous meaning due to evolving of language, precedent cases, or the appearance of new technologies, the meaning of a term used in this disclosure should first be clarified by its usage and/or definition in this disclosure. If further clarification is needed, the term should then be clarified as one of ordinary skill in the art would have understood the term in context of the disclosure at the time of the disclosure.

When a part "includes" or "comprises" an element, unless there is a particular description contrary thereto, the part can further include other elements. The term "unit" in the embodiments of the present disclosure means a software component or a hardware component that performs a specific function. The hardware component may include, for example, a field-programmable gate array (FPGA) or an application-specific integrated circuit (ASIC).

Software component may refer to executable code and/or data used by the executable code in an addressable storage medium. Thus, software components may be, for example, object-oriented software components, class components, and task components, and may include processes, functions, attributes, procedures, subroutines, segments of program code, drivers, firmware, micro codes, circuits, data, a database, data structures, tables, arrays, or variables.

A function provided by a "unit" may be divided into additional components and "units."

Reference will now be made in detail to embodiments, examples of which are illustrated in the accompanying drawings. In this regard, the present embodiments may have different forms and should not be construed as being limited to the descriptions set forth herein.

In the following description, well-known functions or constructions are not described in detail so as not to obscure the embodiments with unnecessary detail.

FIG. 1 is a diagram illustrating an electronic device in accordance with an embodiment of the present disclosure. Referring to FIG. 1, an electronic device, which may be the user-wearable device 100, has a display 102, processors 110 and 112, a sensor module 120, a battery 130, a band 140, and a clasp 142. The sensor module 120 may include sensors 122 and 124. The processor 110 or the processor 112 may also be referred to as a diagnostic processor.

Although the user-wearable device 100 may be worn on a wrist, various embodiments of the disclosure need not be so limited. The user-wearable device 100 may also be designed to be worn on other parts of the body, such as, for example, on an arm (around the forearm, the elbow, or the upper arm), on a leg, on the chest, on the head like a headband, on the throat like a "choker," and on an ear. The user-wearable device 100 may be able to communicate with other electronic devices such as, for example, a smart phone, a laptop, or various medical devices at a hospital or a doctor's office. This will be described in more detail with respect to FIG. 3.

The display 102 may output monitored physiological signals from the user's body for viewing by the user and/or others. The signals being monitored may be referred to as biosignals or biometric data. The monitored signals may be, for example, heart (pulse) rate, pulse morphology (shape), pulse spacing (inter-beat intervals), respiration (breathing) rate, and blood pressure. The display 102 may also output instructions to the user or others in the use of the user-wearable device 100 or use of other measurement devices, as well as status and diagnostic results, for example.

The processor 110 may receive the monitored signals via a low powered sensor in the sensor module 120. The sensor module 120 may include, for example, the sensors 122 and 124 that acquire signals from the user's wrist when the user-wearable device 100 is worn by a user. The sensor 122 and/or 124 may be, for example, an accelerometer. The processor 112 may control the sensors 122 and 124, and may also process the signals monitored by the sensors 122 and 124. For example, the processor 112 may decompose the signals monitored by the sensors 122 and/or 124, and then reconstruct the decomposed signals. Various embodiments of the disclosure may have the processor 110 also perform the functions of the processor 112. Various embodiments of the disclosure may also have different number of sensors.

The sensor 122 may be, for example, a motion sensor or an accelerometer used to continuously or near continuously monitor pulse related information. The sensor 124 may be similar to the sensor 122 or a different type of sensor such as, for example, a thermometer for taking the user's temperature.

The battery 130 may be configured to provide power for the user-wearable device 100. The battery 130 may be charged using a wired charging system or a wireless charging system. The band 140 may be wrapped around a wrist and the user-wearable device 100 may be held on the wrist by using the clasp 142.

Figure 2:
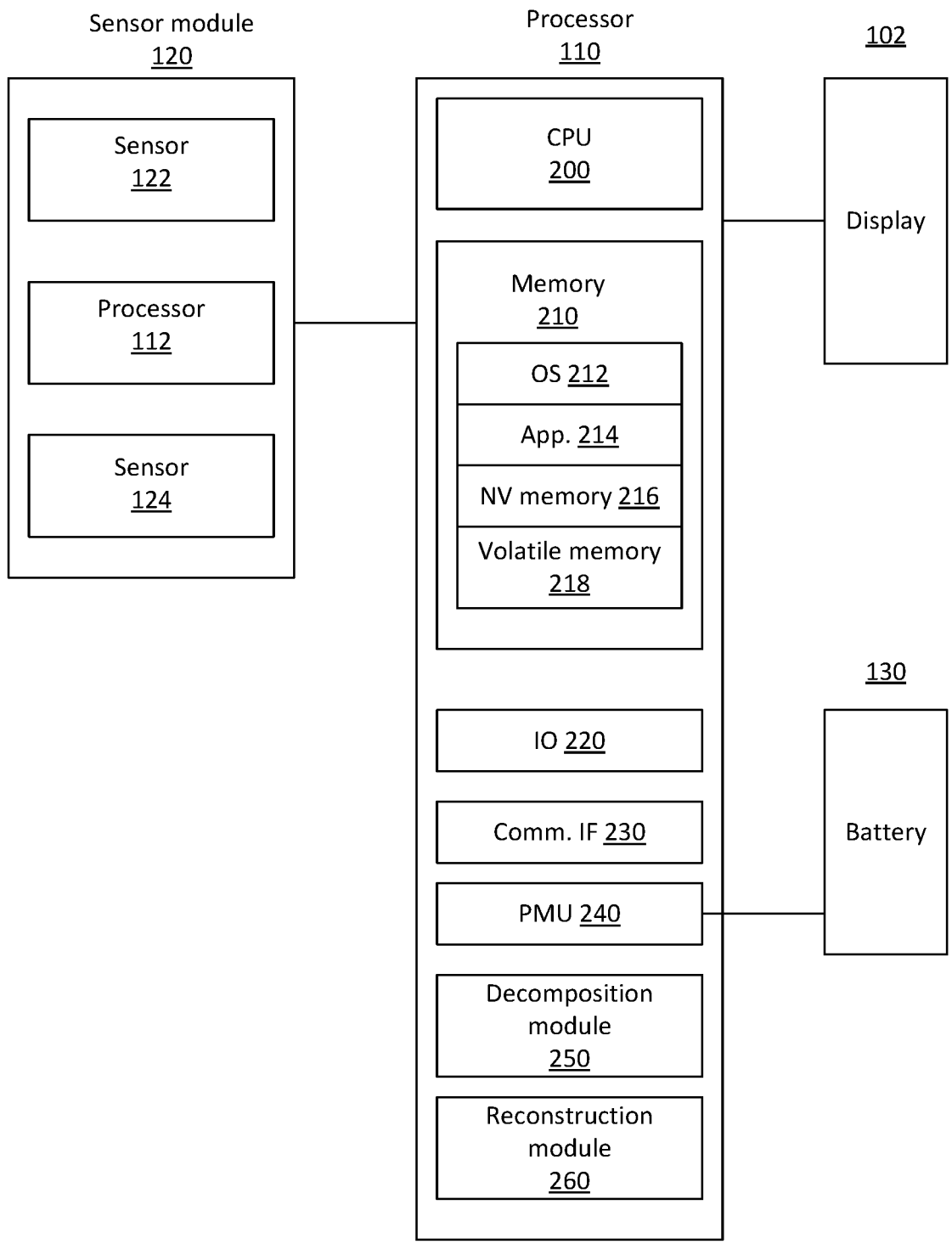
FIG. 2 is a high-level block diagram of an electronic device in accordance with an embodiment of the present disclosure.

FIG. 2 is a high-level block diagram of an electronic device in accordance with an embodiment of the present disclosure. Referring to FIG. 2, there is shown the display 102, the processor 110, the sensor module 120, and the battery 130. Output to the display 102 may be controlled by the processor 110. The display 102 may also include input devices (not shown) such as, for example, buttons, dials, touch sensitive screen, and microphone.

The processor 110 may include a CPU 200, memory 210, an input/output (IO) interface 220, a communication interface 230, a power management unit (PMU) 240, a decomposition module 250, and a reconstruction module 260. While the processor 110 is described as comprising these various devices, other embodiments may use other architectures where the different functionalities are grouped differently. For example, the grouping may be in different integrated circuit chips. Or the grouping may be combining different devices such as the IO interface 220 and the communication interface 230 together, or the decomposition module 250 and the reconstruction module 260 together.

The CPU 200 may control operation of the sensor module 120 as well as receive monitored signals from the sensor module 120. The CPU 200 may control the user-wearable device 100, including processing the monitored signals from the sensor module 120, displaying the processed signals on the display 102, receiving input from the display 102, interfacing with various devices via the IO interface 220 or the communication interface 230 by executing instructions in the memory 210. The IO interface 220 may be used by the CPU 200 to interface with the display 102.

The processor 112 may operate using different architectures in different embodiments. For example, the processor 112 may use the memory 210 to store instructions to execute, or the processor 112 may have its own memory (not shown) for its instructions. Although some embodiments have separate processors 110 and 112, the various embodiments need not be limited so. There may be one processor 110 that controls the functionality of the user-wearable device 100, or there may be multiple processors for the user-wearable device 100.

The memory 210 may include non-volatile memory 216 and volatile memory 218. The operating system and applications may be stored in the non-volatile memory 216. Various embodiments of the disclosure may use different memory architectures that are design and or implementation dependent.

The communication interface 230 may allow the user-wearable device 100 to communicate with other devices via, for example, a wired or wireless protocol such as USB, BLUETOOTH, Near Field Communication (NFC), and WIFI. The PMU 240 may control receiving power from an outside source, charging the battery 130, as well as allocation of power to the different parts of the user-wearable device 100.

The decomposition module 250 may function to decompose, for example, an input signal such as a BCG signal to multiple frequency bands using time-frequency transforms. The reconstruction module 260 may function to reconstruct, for example, the decomposed signals from the decomposition module 250 to refine and access desired components of the original signal such as the BCG signal.

Figure 3:
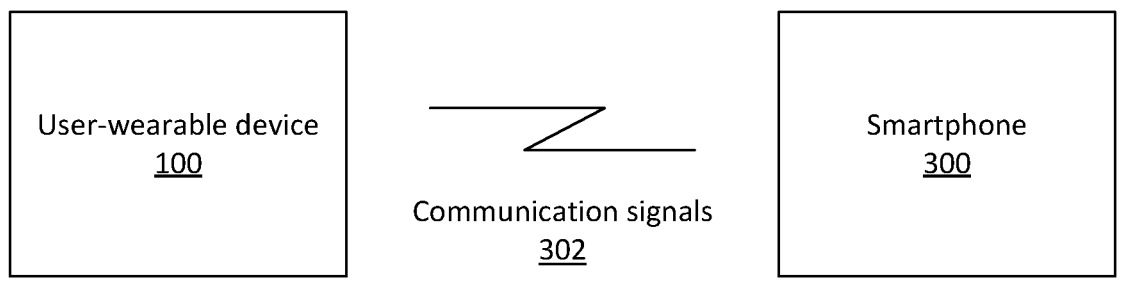
FIG. 3 is an illustration of an electronic device in a communication network in accordance with an embodiment of the present disclosure.

FIG. 3 is an illustration of an electronic device in a communication network in accordance with an embodiment of the present disclosure. Referring to FIG. 3, there is shown the user-wearable device 100 and a smartphone 300. The user-wearable device 100 may communicate with the smartphone 300 using the communication interface 230. The communication may be via the communication signals 302, where the communication may be direct between the user-wearable device 100 and a smartphone 300, or include other elements between the user-wearable device 100 and a smartphone 300.

One of the applications 214 of the user-wearable device 100 may allow the smartphone 300 to control at least some operation of the user-wearable device 100. For example, user-wearable device 100 may output to the display 102 a result of the processing by the processor 110, and/or the same result may be transmitted to the smartphone 300. The user may also select an option either on the user-wearable device 100 or on the smartphone 300. The options may be, for example, to start a biosignal monitoring process by the user-wearable device 100 or to stop the biosignal monitoring process.

Since the smartphone 300 has a larger display, it may be easier for the user to view a result or to select an option on the smartphone 300 rather than on the user-wearable device 100. However, it should be noted that the smartphone 300 may not generally be necessary for operation of the user-wearable device 100.

Figure 4A:
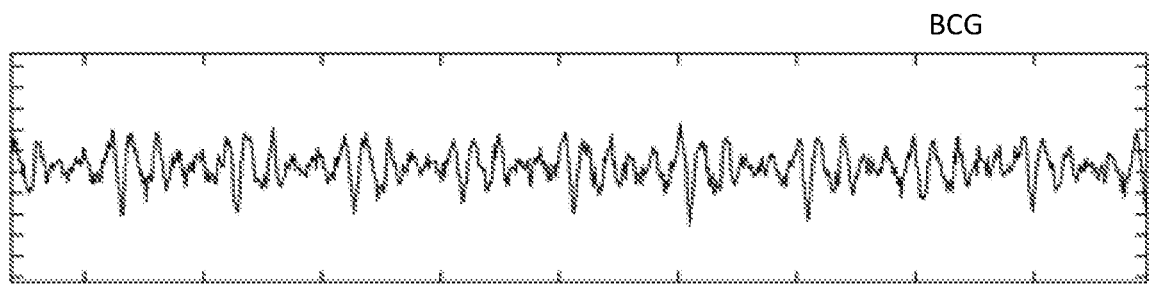
FIG. 4A is an exemplary illustration of BCG signals in accordance with an embodiment of the present disclosure.
Figure 4B:
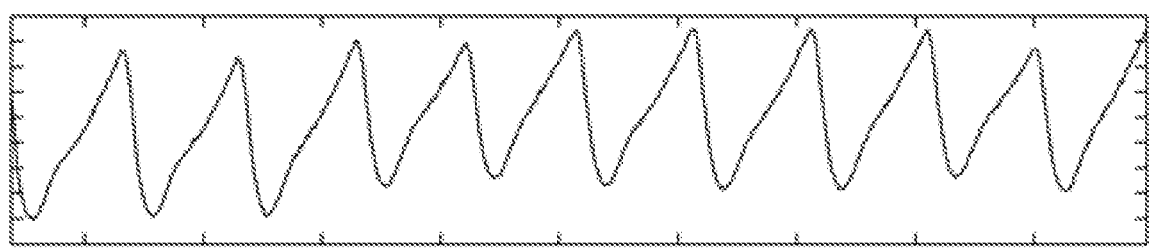
FIG. 4B is an exemplary illustration of PPG signals in accordance with an embodiment of the present disclosure.

FIGS. 4A and 4B illustrate BCG signals and PPG signals, respectively. BCG signals measure body acceleration caused by cardiac output as well as respiration movements. Typically, BCG signals correspond to movements coaxial with the human body. As can be seen, the PPG signal in FIG. 4B is relatively simple while the BCG signals in FIG. 4A is relatively complex in that a BCG signal contains multiple peak events during one heartbeat. The peaks can be categorized into three major groups: pre-systolic, systolic and diastolic. Due to the complexity of the BCG signal and the harmonic pattern of the BCG signal, it may be challenging to determine a heart rate and a respiration rate directly from a raw BCG signal. Accordingly, the BCG signal may need to be processed to determine the heart rate, and respiration rate.

An ideal BCG signal may be modeled as:

$$BCG(t) = A \cdot \sin\left(\frac{2\pi f_{HR} t}{k}\right) \cdot \sin(2\pi f_{HR} t) \cdot (B \cdot \sin(2\pi f_{RR} t + \varphi)) + \delta \quad (1)$$

where A refers to a weight of cardiac-related components, B refers to a weight of respiratory components, $f_{HR}$ refers to a heartbeat frequency, $f_{RR}$ refers to a respiration frequency, k refers to a harmonic factor of heart beat, φ refers to a respiratory phase shift, and δ refers to noise and artifacts.

In order to accurately quantify cardiac and respiratory activity using BCG signals, the present disclosure provides a BCG transformation process (signal pre-processing) to extract corresponding parameters from Equation (1) and convert the parameters into a PPG-like waveform. This is explained in more detail below.

While various embodiments of the disclosure have been disclosed to determine heart rate and respiration rate, the embodiments need not be so limited. For example, the BCG signals may also be processed determine the respiration phases of a user.

Figure 5A:
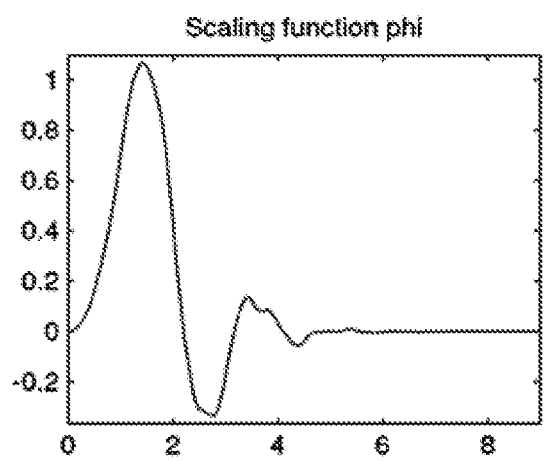
FIG. 5A illustrates exemplary Daubechies 5 scaling function waveform in accordance with an embodiment of the present disclosure.
Figure 5B:
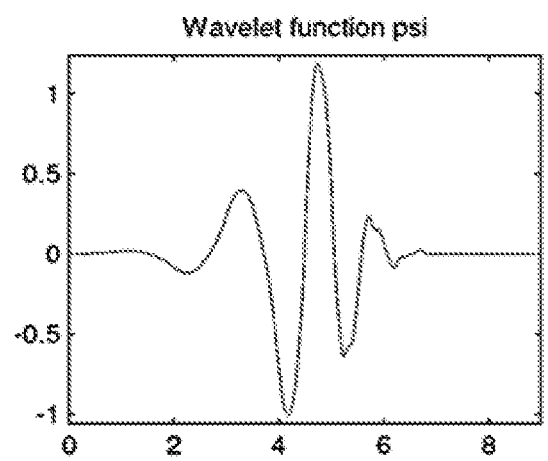
FIG. 5B illustrates exemplary Daubechies 5 wavelet function waveform in accordance with an embodiment of the present disclosure.

FIGS. 5A and 5B illustrates exemplary Daubechies 5 scaling function waveform and Daubechies 5 wavelet function waveform, respectively. An embodiment of the disclosure may use the scaling function and the wavelet function shown to decompose a signal such as, for example, a BCG signal.

FIGS. 6A-6I illustrate an exemplary BCG signal and the wavelet-based BCG decomposition waveforms in accordance with an embodiment of the present disclosure. These figures illustrate the BCG signal in FIG. 6A and the eight frequency bands resulting from decomposition of the BCG signal by seven levels of decomposition. For example, FIGS. 6B-6I may show a BCG signal of 100 Hz sampling rate decomposed into 8 frequency bands. The 8 frequency bands shown in FIGS. 6B-6I correspond to frequency bands of substantially 0 to 0.78 Hz, 0.78 to 1.56 Hz, 1.56 to 3.13 Hz, 3.13 to 6.25 Hz, 6.25 to 12.5 Hz, 12.5 to 25 Hz, 25 to 50 Hz, and 50 to 100 Hz, respectively.

The lower frequency layers may correspond to respiratory patterns while medium frequency bands may correspond to heartbeat events. The Daubechies 5 waveforms shown in FIGS. 4A and 4B may be used to decompose the BCG signal shown in FIG. 6A to the decomposed signals shown in FIGS. 6B-6I since the Daubechies 5 wavelet has high similarity with BCG beat events.

Various embodiments of the present disclosure may perform BCG signal decomposition based on other wavelets such as, for example, a Symlet wavelet or a biorthogonal wavelet, that show high correlation with a BCG beat event. Other embodiments may provide a configurable wavelet that refers to a BCG (morphology). Accordingly, various embodiments may use different types of wavelets, including, for example, a self-generated mother wavelet.

While eight frequency bands were shown in FIGS. 6B to 6I for the decomposed BCG signal, the number of decomposed frequency bands may be any number based on the BCG sampling rate and the specified use case (e.g., heart rate, respiration rate, respiration phases, blood pressure) without deviating from the scope of the present disclosure.

Various embodiments of the disclosure may make a desired type of rate measurement from a user's body based on an associated frequency band. Accordingly, the sensor data may be acquired from various body locations of the user.

Various embodiments of the disclosure may perform BCG signal decomposition based on one or more of a plurality of signal decomposition techniques, including, but not limited to Hilbert transform, one or more finite impulse response (FIR)/infinite impulse response (IIR) filters with different cut-off frequencies and stop bands, a time-domain based moving average method and multi-order derivatives.

Figure 7A:
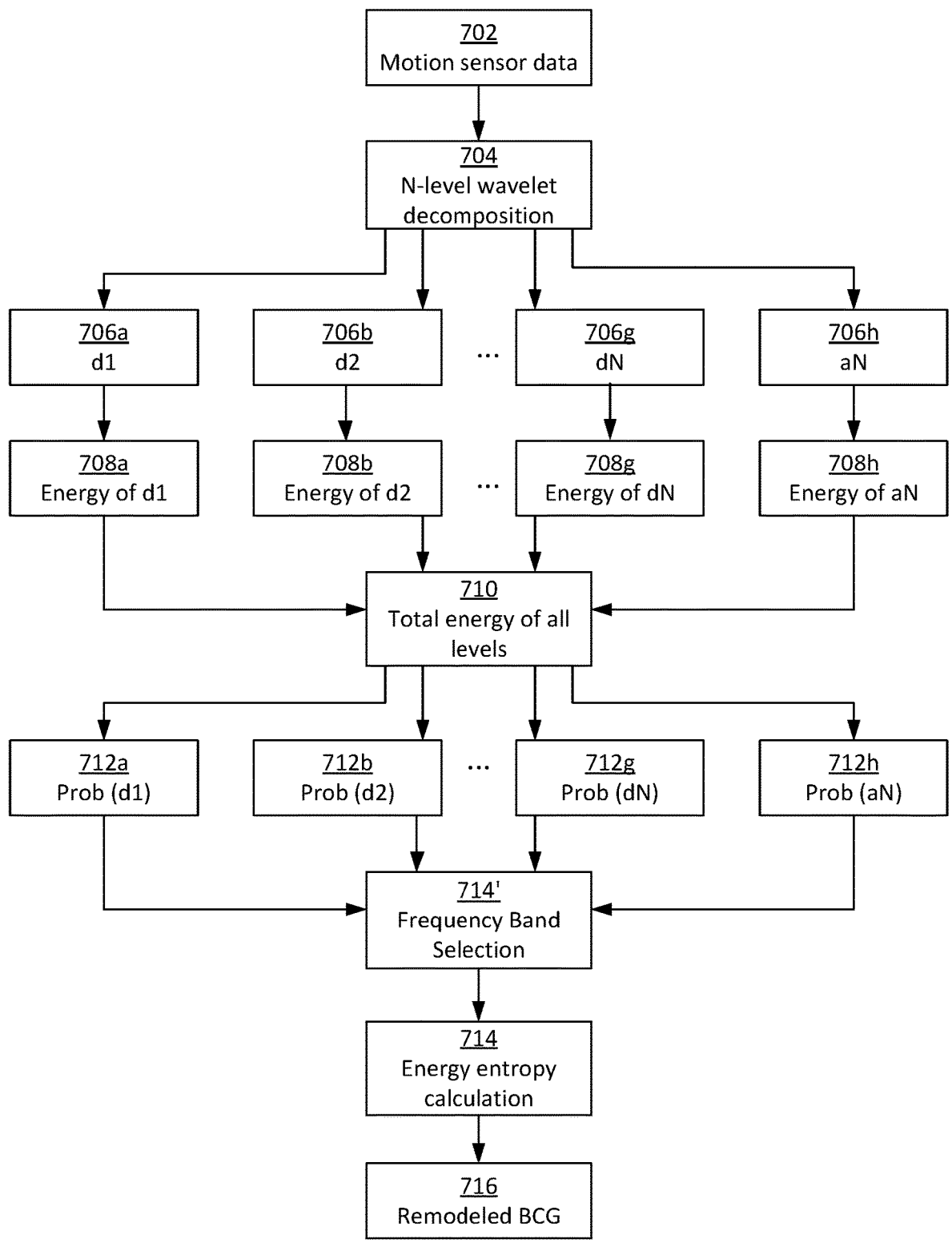
FIG. 7A illustrates an exemplary flowchart for reconstructing decomposed BCG signals in accordance with an embodiment of the present disclosure.

FIG. 7A illustrates an exemplary flowchart for reconstructing decomposed BCG signals in accordance with an embodiment of the present disclosure. Referring to FIG. 7A, various sensors, such as, for example, the sensors 122 and/or 124, may detect motion in one or more directions. For example, each of the sensors 122 and 124 may be able to detect motion in X, Y, and Z directions. Alternatively, a sensor on the wearable device 100 may be able to detect motion in only one or two directions. A sensor able to detect motion in multiple directions may be said to have multiple channels where each channel may detect motion in a specific direction. BCG can be interpreted as single channel motion sensor signal or multi-channel fusion signal (e.g. accelerometer magnitude signal). The motion sensor may detect, for example, acceleration.

The motion data may be received at 702. This motion data may be, for example, the acceleration magnitude as shown in the BCG signal of FIG. 4A. At 704 the motion data may be decomposed using N-level wavelet decomposition. The decomposition may be performed, for example, by the decomposition module 250. This may result in the decomposed signals shown at 706a to 706h, corresponding to the decomposed signals shown in FIGS. 6B-6I.

Various embodiments of the disclosure may apply, for example, one or more statistical averaging methods for the re-construction process to refine and enhance deterministic components of the decomposed BCG signal. For example, a moving average energy entropy based may be used. A sliding window may be used to calculate moving average energy. In each window instance, energy-entropy is described in Equations (2)-(4) given below. A sliding window with a desired window size based on a specific use case may be used. Additionally, multi-window based re-construction may be applied based on specific use cases.

At 708a to 708h, an energy calculation may be made for each of the decomposed signals shown at 706a to 706h. Depending on the architecture, the calculations may be made by the decomposition module 250, the reconstruction module 260, the processor 112, and/or the CPU 200. Other architectures not shown may use other processors. The energy calculation may use Equation (2):

$$\text{Energy}_i = \text{sum}(i\text{th Decomposed signal})^2 \quad (2)$$

At 710, the individual energy levels may be collected to calculate the probability distribution of the decomposed signals 706a-706h. The individual probability may be calculated using Equation (3):

$$\text{Prob}_i = \frac{\text{Energy}_i}{\sum_{k=1}^{N} \text{Energy}_k} \quad (3)$$

The individual probabilities at 712a to 712h may then be used to calculate the entropy S of the signals, as shown in Equation (4):

$$S = -\sum_{i=1}^{N} \text{Prob}_i \cdot \ln(\text{Prob}_i) \quad (4)$$

Various embodiments may use the entropy S to calculate the Boltzmann entropy $S_B$ to reconstruct a reconstructed signal from the decomposed signals 706a-706h:

$$S_B = -Nk_B \sum_{i=1}^{N} \text{Prob}_i \cdot \ln(\text{Prob}_i) \quad (5)$$

By adjusting the Boltzmann constant $k_B$, various embodiments of the present disclosure may develop an adaptive weight for each sliding window. Accordingly, the various embodiments may further provide time domain smoothing techniques including, but not limited to, moving average and maximum modulus principle based on specific use cases.

At 714', one or more frequency bands corresponding to, for example, 706a to 706h may be selected. At 714, Equations (4) and (5) may be used to make energy entropy calculations of the selected frequency bands. The energy entropy calculations may then be used at 716 to reconstruct the BCG signal from the decomposed BCG signal in order to enhance and recover, for example, a heart rate, respiration phases, and a respiration rate. In some embodiments of the disclosure, no reconstruction may be needed for respiration. Various embodiments may use lower frequency bands, such as the VLF bands for determining respiration rates and/or phases of respiration.

While specific modules have been described as performing specific functions, the scope of the disclosure need not be limited so. For example, the decomposing and reconstructing may be performed by a common hardware and/or software module. The software module may include instructions that are executed by a processor such as the processor 110 and/or 112.

Figure 7B:
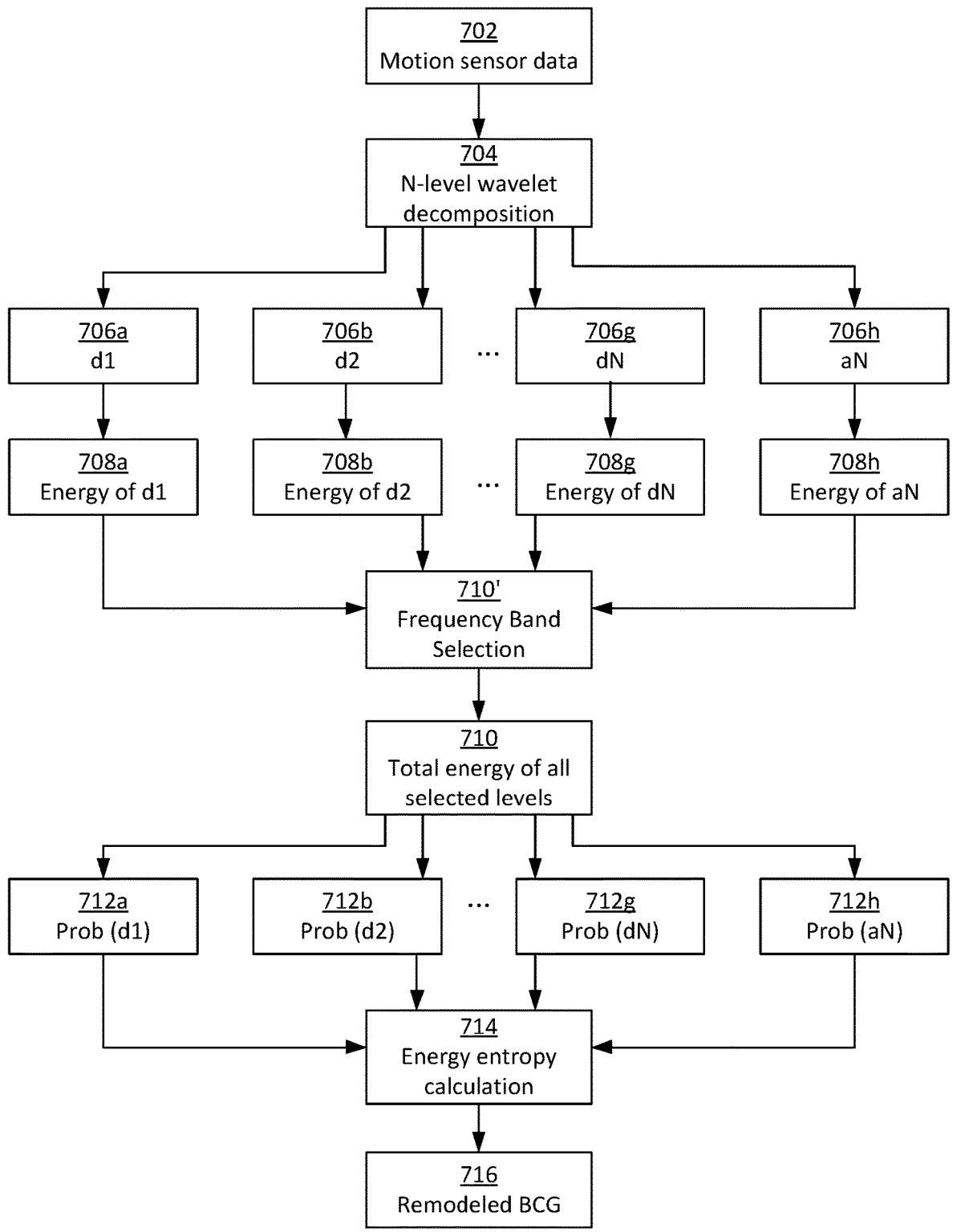
FIG. 7B illustrates an exemplary flowchart for reconstructing decomposed BCG signals in accordance with an embodiment of the present disclosure.

FIG. 7B illustrates an exemplary flowchart for reconstructing decomposed BCG signals in accordance with an embodiment of the present disclosure. The similar portions of FIG. 7B and FIG. 7A, for example, 702, 704, 706a . . . 706h, and 708a . . . 708h, will not be described. After 708, frequency band selection occurs at 710' prior to 710. Accordingly, at 710 the individual energy levels may be collected for the selected frequency bands to calculate the probability distribution of the selected decomposed signals 706a-706h. The individual probabilities for the selected frequency bands may be calculated using Equation (3).

The individual probabilities of the selected frequency bands of 712a to 712h may then be used to calculate the entropy S of the signals, as shown in Equation (4). At 714, Equations (4) and (5) may be used to make energy entropy calculations of the selected frequency bands. The energy entropy calculations may then be used at 716 to reconstruct the BCG signal from the decomposed BCG signal in order to enhance and recover, for example, a heart rate, respiration phases, and a respiration rate. In some embodiments of the disclosure, no reconstruction may be needed for respiration.

FIGS. 8A-8F illustrate exemplary waveforms of reconstructed BCG signals in accordance with an embodiment of the present disclosure. For comparison, FIGS. 8A-8C illustrate exemplary waveforms of reconstructed signals with good signal quality and FIGS. 8D-8F illustrate exemplary waveforms of reconstructed signals with bad signal quality.

As shown in FIGS. 8A-8F, the BCG signal re-construction significantly suppresses cardiac harmonic components and high frequency artifacts for a wide range of BCG signals. In all stationary cases, re-constructed BCG signals may be highly correlated with PPG signals from a PPG sensor. Information from the reconstructed BCG signals may be further extracted for downstream methods to determine heart rate variability (HRV), sleeping quality, and stress. An advantage of BCG reconstruction is that multiple heartbeat harmonics and ambiguities are removed.

According to some embodiments, the BCG signals may be converted into a PPG-like waveform based on a pre-defined frequency transfer function between the BCG signals and desired PPG signals. The pre-defined frequency transfer function may be based on comparing a frequency response of BCG signals and corresponding desired PPG signals and quantifying their frequency relation. The pre-defined transfer function may be used to specify filter parameters for BCG transformation.

Figure 9A:
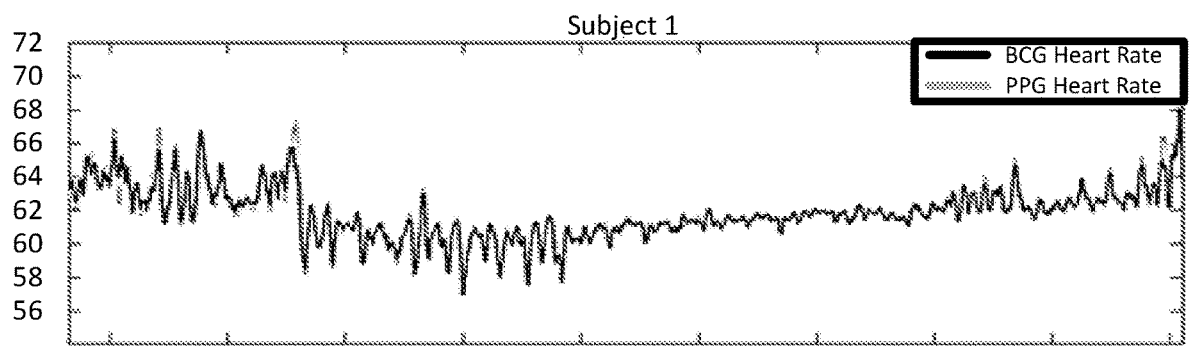
FIG. 9A illustrates exemplary waveforms for BCG based and PPG based heart rate trends for a first user in accordance with an embodiment of the present disclosure.
Figure 9B:
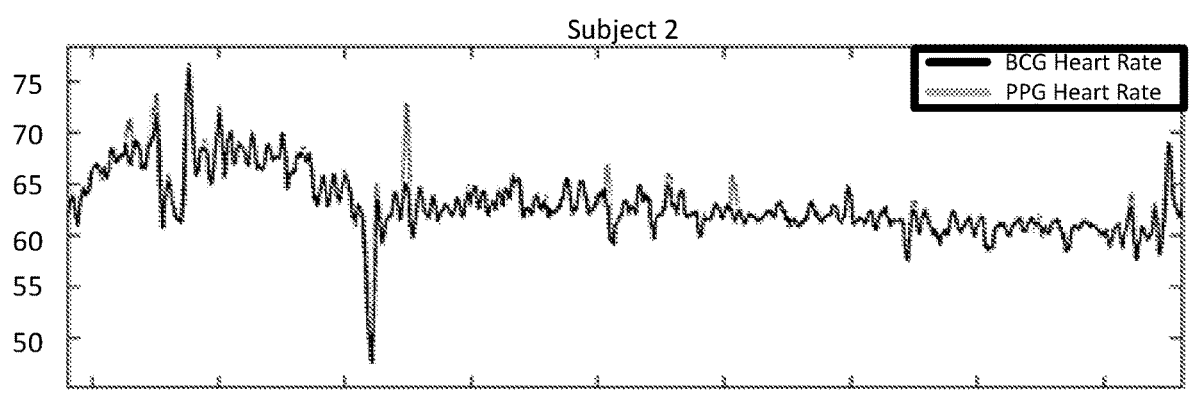
FIG. 9B illustrates exemplary waveforms for BCG based and PPG based heart rate trends for a second user in accordance with an embodiment of the present disclosure.

FIGS. 9A and 9B illustrate exemplary waveforms for BCG based and PPG based heart rate trends for two users in accordance with an embodiment of the present disclosure. As can be seen in each of the FIGS. 9A and 9B, the present BCG-based overnight heart rates of two subjects (users) are highly identical with optical sensor (PPG) based heart rate trends.

Some embodiments may apply fast Fourier transformation to the re-constructed BCG signal with a sliding time window. In each window, the first N largest peaks in a spectrum may be extracted as heart rate candidates. A biosemantic heart rate tracking mechanism such as that previously disclosed in U.S. application Ser. No. 14/924,565 may be used to continuously track a user's heart rate. The U.S. application Ser. No. 14/924,565 is incorporated in its entirety by reference.

Some embodiments may further extract BCG-based heart rate candidates based on a number of different methods. One method includes applying Cepstrum analysis on re-constructed BCG or raw BCG signals to identify harmonic delays. These maxima values may be considered as the fundamental frequency of a given segment of the signal. Some embodiments may apply non-linear signal re-construction based on projecting the re-constructed BCG signal into a specified attractor with given embedding dimension and time delay. The recurrence plot analysis may then be used to identify periodic cardiac activity patterns.

So far, various embodiments have been described that use a magnitude vector of a sensor, such as a tri-axis accelerometer, as a BCG signal for heart rate estimation. Other embodiments may be able to detect respiration rate from the very low frequency (VLF) band from the BCG signal as illustrated in FIG. 6B. As the magnitude vector of the BCG signal suppresses DC/low frequency components, the single axis of the accelerometer may be used for estimation of respiration rate. However, a multiple-axes accelerometer fusion can also be used to determine respiratory events.

Figure 10:
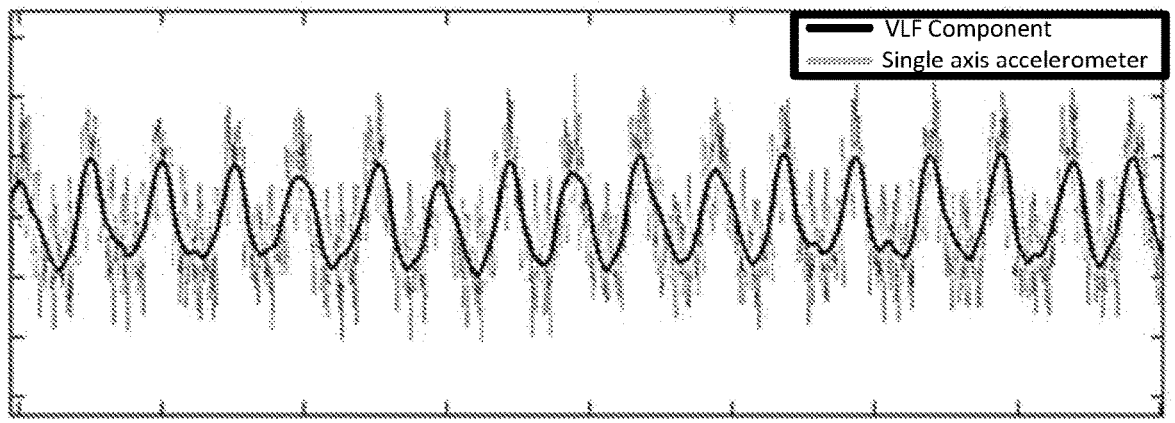
FIG. 10 illustrates exemplary waveform of a signal from a sensor versus a very low frequency (VLF) component of the corresponding signal in accordance with an embodiment of the present disclosure.

FIG. 10 illustrates exemplary waveform of a signal from a single axis of an accelerometer versus a VLF component of the corresponding signal in accordance with an embodiment of the present disclosure. As can be seen, the VLF component tracks the waveform of a signal from a single axis of an accelerometer very well. This indicates that no appreciable error is introduced while decomposing the original signal such as the BCG signal in FIG. 6A. Therefore, various embodiments may also perform similar tracking using the mechanism described earlier to continuously track a user's respiration rate.

Figure 11A:
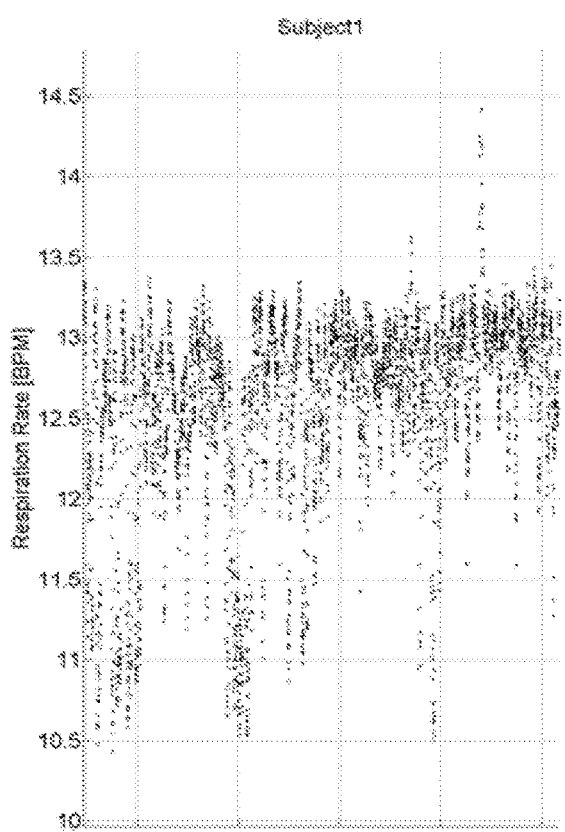
FIG. 11A illustrates exemplary waveforms of overnight respiratory rate trends of a first user in accordance with an embodiment of the present disclosure.
Figure 11B:
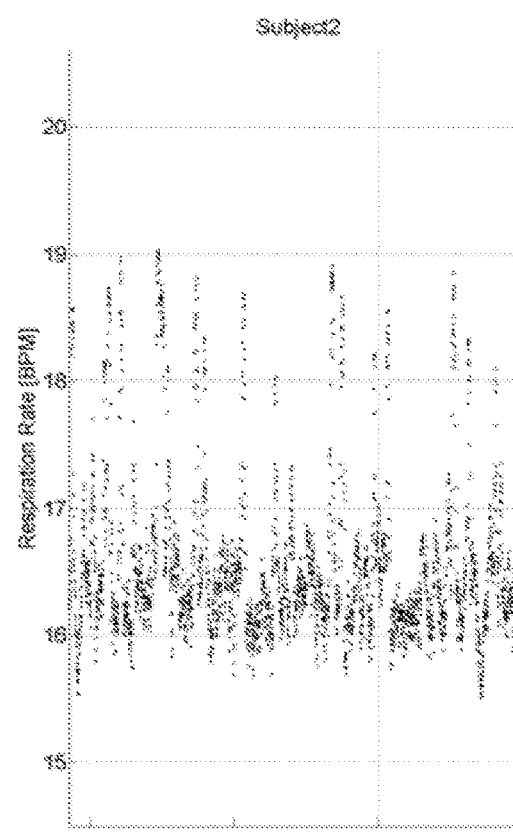
FIG. 11B illustrates exemplary waveforms of overnight respiratory rate trends of a second user in accordance with an embodiment of the present disclosure.

FIGS. 11A and 11B illustrate exemplary waveforms of overnight respiratory rate trends of two users in accordance with an embodiment of the present disclosure. Respiration rates can be determined using BCG waveforms in various embodiments of the disclosure. Heartbeat events may also be causally modulated by respiratory events.

Figure 12:
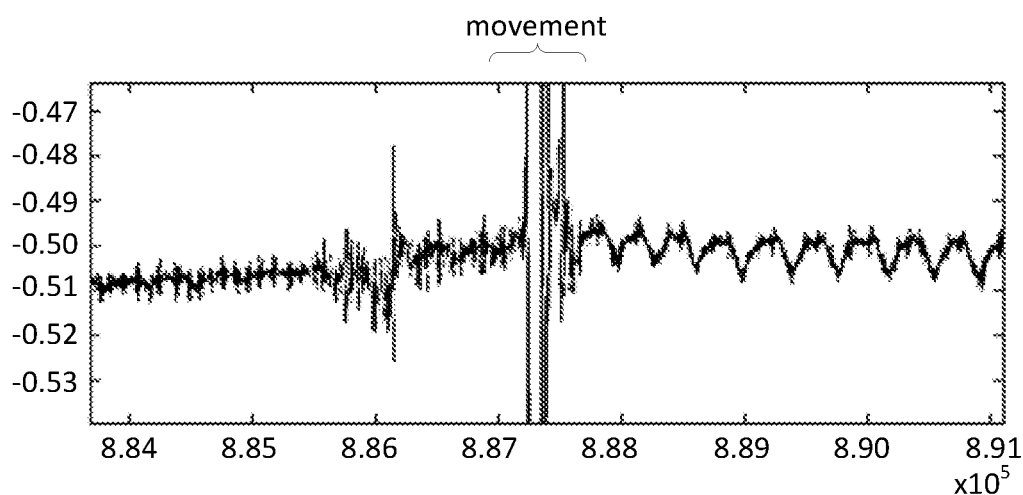
FIG. 12 illustrates an exemplary waveform of signal quality variation triggered by orientation change of a sensor in accordance with an embodiment of the present disclosure.

FIG. 12 illustrates an exemplary waveform of signal quality variation triggered by orientation change of a sensor in accordance with an embodiment of the present disclosure. It can be seen that there is movement near the center of the graph in FIG. 12, and that the signals monitored after the movement is different from the signals monitored before the movement. This is an example of how having a sensor in different positions or orientations can affect signal quality.

In order to obtain the best accuracy performance, various embodiments of the disclosure may apply a smart motion sensor channel selection mechanism. When motion is detected, a motion sensor channel reset flag may be triggered. An embodiment may then re-select an motion sensor channel for a subsequent respiration rate estimation cycle. The channel evaluation criteria may be based on a respiration rate estimation confidence indicator where the presence of a dominant peak in a spectrum of VLF of a given axis can be considered as high respiration rate quality confidence. The channel evaluation criteria may also be based on a heart rate estimation confidence indicator where the presence of a dominant peak in a spectrum of reconstructed BCG signal may indicate high heart rate quality confidence.

Figure 13A:
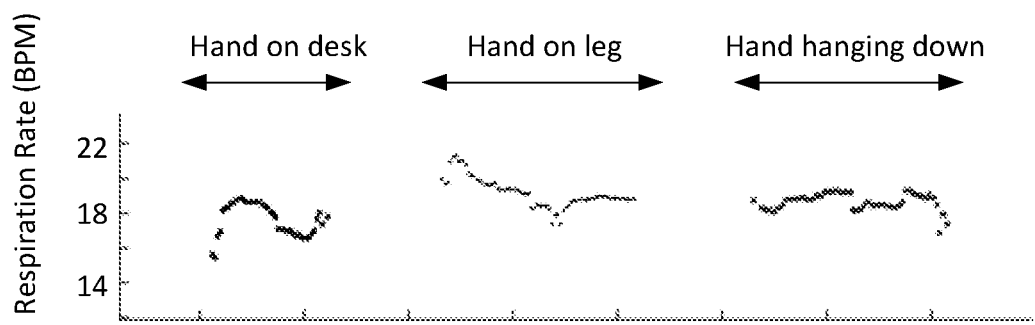
FIG. 13A illustrates exemplary waveforms of respiration rate estimations under various hand positions in accordance with an embodiment of the present disclosure.
Figure 13B:
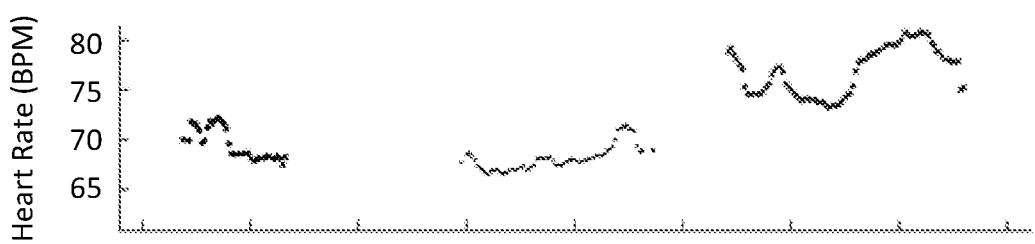
FIG. 13B illustrates exemplary waveforms of heart rate estimations under various hand positions in accordance with an embodiment of the present disclosure.

FIGS. 13A and 13B illustrate exemplary waveforms of heart rate and respiration rate estimations under various hand positions in accordance with an embodiment of the present disclosure. FIGS. 13A and 13B show that when BCG is measured from a user's wrist when the user's hand is in various positions (e.g., hand on desk, hand on leg, and hand hanging down), the estimated heart rate and respiration rate remains robust. Accordingly, it should be appreciated that BCG signals may be acquired from different parts of a user's body (e.g., forehead, ear, chest, leg, and arm) without deviating from the scope of the present disclosure.

According to various embodiments, a low power motion sensor such as an accelerometer sensor may be used instead a PPG sensor for continuous resting heart rate monitoring, since the PPG sensor may consume significantly more power than the motion sensor. Accordingly, the use of low power motion sensor as disclosed may significantly prolong a battery charging cycle. Consider the following system power consumption equation.

$$E(t)=E_0-\epsilon_0-S_{bg}t-K_1S_{ppg}t-K_2S_{base}t-K_3S_{accel}t \quad (6)$$

where $E_0$ refers to an initial state of battery energy (in Joules), $\epsilon_0$ refers to a battery energy safety margin (in Joules), $S_{bg}$ refers to power drain from the background monitoring process (in Watts), $S_{ppg}$ refers to an average power drain during PPG sampling (in Watts), $S_{base}$ refers to an average power drain of a base module including the motion sensor or the accelerometer during wakeup of a accelerometer-device (in Watts), $K_1$ refers to a PPG sampling duty cycle, $K_2$ refers to a base module wakeup duty cycle, $K_3$ refers to an accelerometer sampling duty cycle, and t refers to a time variable (in seconds).

For continuous heart rate and respiration rate monitoring, $K_1$ and $K_3$ are equal to 1, and Equation (6) may be simplified as follows:

$$E(t)=E_0-\epsilon_0-S_{bg}t-S_{ppg}t-K_2S_{base}t-S_{accel}t \quad (7)$$

It may be observed that the base module duty cycle $K_2$ depends on the complexity of the processes running on the base module. If the processes running on the base module is very efficient, $K_2$ can be a very small fraction number. In this case, battery running time is the time till the battery has been drained:

$$t = \frac{E_0 - \epsilon_0}{S_{bg} + S_{ppg} + K_2S_{base} + S_{accel}} \quad (8)$$

Assuming $S_{ppg}=k \cdot (S_{bg}+K_2S_{base}+S_{accel})$ and $K_2$ is a constant value:

$$\frac{t_{BCG}}{t_{PPG}} = \frac{(k+1) \cdot (S_{bg} + K_2S_{base} + S_{accel})}{(S_{bg} + K_2S_{base} + S_{accel})} = k+1 \quad (9)$$

Based on Equation (9), the battery charging cycle can be prolonged by as much as k times by switching to BCG-based resting heart rate and respiration rate estimation. Also, respiration rate accuracy can be seen to be significantly improved. Various embodiments of the presently disclosed BCG-based continuous heart rate/respiration rate estimation system have prolonged a battery cycle by at least 300% as compared to a PPG-based system.

According to various embodiments of the disclosure, the battery cycle may be further extended based on one or more smart power scheduling mechanisms. One smart power scheduling mechanism allows the present system to acquire daytime heart rate and respiration rate measurements intermittently during still periods between typical daily motions. Another smart power scheduling mechanism allows sleeping heart rate and respiration rate to be continuous trends that are only interrupted by short periods of wakefulness.

Large amounts of daytime resting periods may provide insights into a user's resting heart rate trends. They are meaningful for use cases such as stress analysis and hypertension monitoring. On the other hand, continuous sleeping trends provide valuable information about HRV, sleeping disorder, and cardiac arrhythmia.

Figure 14A:
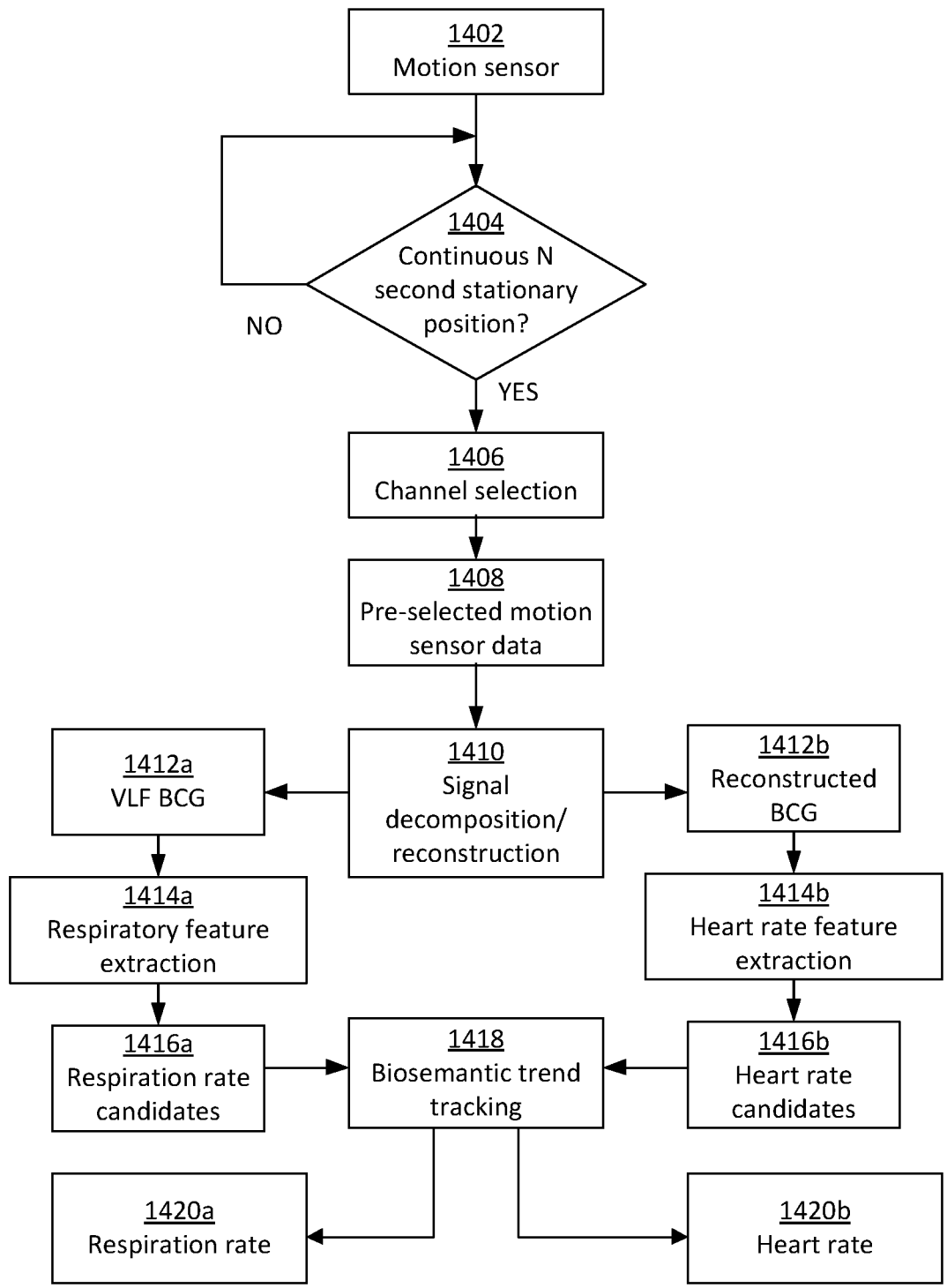
FIG. 14A illustrates an exemplary flow chart for smart power scheduling for continuous resting heart rate and respiration monitoring in accordance with an embodiment of the present disclosure.

FIG. 14A illustrates an exemplary flow chart for smart power scheduling for continuous resting heart rate and respiration monitoring in accordance with an embodiment of the present disclosure. Referring to FIG. 14, one or more sensors, such as, for example, the sensors 122 and/or 124, may detect motion in the X, Y, and Z directions. The motion sensed may be, for example, X, Y, and Z accelerations. Alternatively, a sensor on the wearable device 100 may be able to detect motion in only one or two directions.

The motion may be sensed at 1402. This motion data may be, for example, the BCG signal shown in FIG. 4A. At 1404, a determination may be made whether the wearable device 100 has been in a stable position for a pre-determined period of time. If not, 1404 may be repeated until the wearable device has been in a stable position for the pre-determined period of time. Various embodiments of the disclosure may have a time delay that may be pre-determined or variably set before checking again. If the wearable device 100 has been in a stable position for a pre-determined period of time, 1406 may be next.

At 1406, a channel may be selected for the upcoming biosignal measurements. The channel selection may include analyzing monitored signals to select for the best of the channels. Some embodiments of the disclosure may not search for the best channel, but may stay with the present channel, or go to the next channel of the available channels.

At 1408, signals may be received from the selected channel and the magnitude of the motion, for example, acceleration, may be used to determine the BCG signal. This may be similar to 702 of FIG. 7A or FIG. 7B. At 1410, the signal from 1408 may be decomposed, and the decomposed signal reconstructed as described previously. 1410 may be similar to 704 to 716.

At 1412a, the VLF band of the decomposed signal may be selected for respiration rate monitoring. At 1412b, the reconstructed signal may be selected for heart rate monitoring. At 1414a, respiration rate features may be detected from the VLF band. At 1414b, heart rate features may be detected from the reconstructed signals.

At 1416a, one or more respiration rate candidates may be selected for further processing. At 1416b, one or more heart rate candidates may be selected for further processing. At 1418, a biosemantic trend tracking may determine the heart rate and the respiration rate. At 1420a and 1420b, the determined respiration rate and heart rate, respectively, may be, for example, displayed for the user or others to see. Or the determined respiration rate and heart rate may be communicated to another device, such as, for example, the smartphone 300.

Figure 14B:
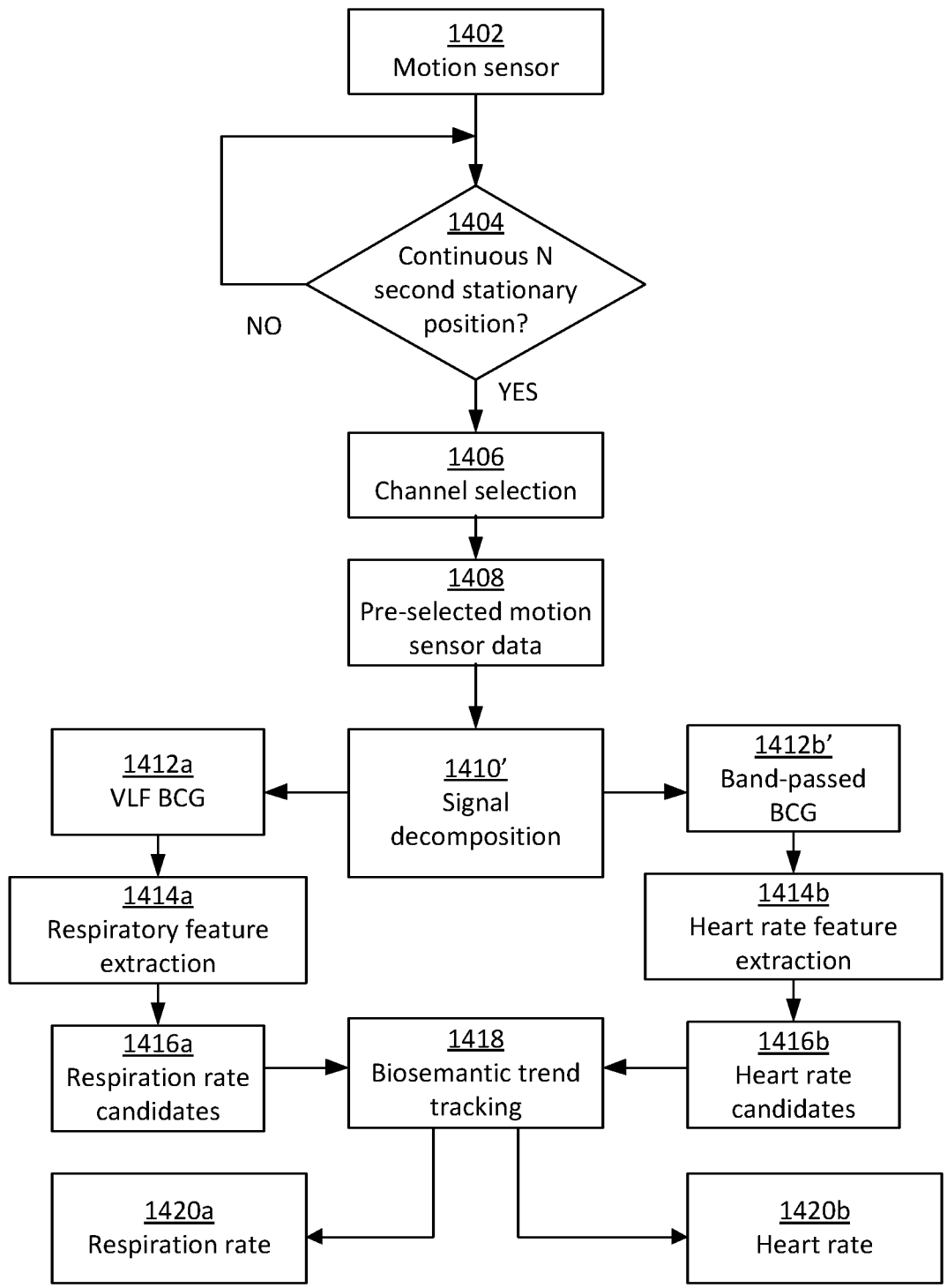
FIG. 14B illustrates an exemplary flow chart for smart power scheduling for continuous resting heart rate and respiration monitoring in accordance with an embodiment of the present disclosure.

FIG. 14B illustrates an exemplary flow chart for smart power scheduling for continuous resting heart rate and respiration monitoring in accordance with an embodiment of the present disclosure. The flow chart of FIG. 14B is similar to the flow chart of FIG. 14A. Accordingly, the initial similar portions of FIG. 14B to FIG. 14A, for example, 1402, 1404, 1406, and 1408, will not be described again. At 1410', the signal from 1408 may be decomposed, but not reconstructed as was done at 1410 of FIG. 14A. At 1412a, the VLF band of the decomposed signal may be selected for respiration rate monitoring. At 1412b', the band-passed signal may be selected for heart rate monitoring, whereas the reconstructed signal was selected for heart rate monitoring in 1412b of FIG. 14A. It may be noted that 1414a, 1414b, 1416a, 1416b, 1418, 1420a, and 1420b are similar as in FIG. 14A.

While the smartphone 300 may have been mentioned as an example of an electronic device with which the wearable device 100 may communicate, various embodiments of the disclosure may communicate with other electronic devices such as those that may be present in a hospital or a doctor's office.

Various embodiments have described the user-wearable device 100 to be directed to monitoring some of a user's biosignals or biometric data. However, other embodiments may monitor different biosignals than those mentioned in this disclosure.

Various embodiments of the disclosure may be written as computer programs and may be implemented in general-use digital computers that execute the programs using a non-transitory computer-readable recording medium.

Non-transitory computer-readable recording medium may include, for example, magnetic storage media (e.g., ROM, floppy disks, and hard disks), and optical recording media (e.g., CD-ROMs, or DVDs).

While various embodiments of the disclosure have been described with reference to the figures, it will be understood by those of ordinary skill in the art that various changes in form and details may be made therein without departing from the spirit and scope of the disclosure as defined by the following claims. Accordingly, the above embodiments and all aspects thereof are examples only and are not limiting.

What is claimed is:

1. A system for measuring biological signals of a user, comprising:
    a sensor module configured to acquire ballistocardiogram (BCG) signals of the user via a present channel, wherein the present channel is at least one channel of the sensor module;
    a decomposition module configured to decompose the BCG signals into decomposed signals;
    a reconstruction module configured to reconstruct at least a portion of the decomposed signals into reconstructed signals using a probability distribution of the decomposed signals;
    a processing module configured to process the reconstructed signals to at least one of a heart rate, a respiration rate, phases of respiration, and a blood pressure; and
    a display configured to display at least one output corresponding to the at least one of the heart rate, the respiration rate, the phases of respiration, and the blood pressure,
    wherein the processing module comprises a diagnostic processor configured to select a next channel when motion is detected by the present channel, wherein the next channel and the present channel are channels of a same accelerometer in the sensor module, and
    wherein:
        the reconstruction module is configured to reconstruct the decomposed signals into reconstructed signals using time domain smoothing based on one or both of moving averages and the maximum modulus principle, and
        during reconstruction, the diagnostic processor is configured to convert the BCG signals using a pre-defined frequency transfer function between the BCG signals and photoplethysmogram (PPG) signals.

2. The system of claim 1, wherein the decomposition module is configured to decompose the BCG signals using a function corresponding to one or more of a wavelet, a Hilbert transform, one or more finite impulse response (FIR)/infinite impulse response (IIR) filters with respective cut-off frequencies and stop bands, a time-domain based moving average, and multi-order derivatives.

3. The system of claim 1, wherein the reconstruction module is configured to reconstruct the at least portion of the decomposed signals using statistical averaging.

4. The system of claim 1, wherein the diagnostic processor is configured to determine the heart rate based on Cepstrum analysis of at least one of the BCG signals and the reconstructed signals.

5. The system of claim 1,
    wherein channel evaluation criteria for selecting the next channel is based on at least one of a respiration rate estimation confidence indicator determined by peaks in a very low frequency (VLF) band of the channel and a heart rate estimation confidence indicator determined by peaks in a spectrum of the reconstructed signals.

6. The system of claim 1, wherein the probability distribution is determined based on an energy contained in each of the decomposed signals.

7. A non-transitory machine-readable medium storing machine executable instructions that when executed cause a computing system to control operations for measuring biological signals of a user, the operations comprising:
    acquiring ballistocardiogram (BCG) signals of the user via a present channel, wherein the present channel is at least one channel of a sensor module;
    decomposing the BCG signals into decomposed signals;
    reconstructing at least a portion of the decomposed signals into reconstructed signals using a probability distribution of the decomposed signals;
    processing the reconstructed signals to at least one of a heart rate, a respiration rate, phases of respiration, and a blood pressure;
    displaying at least one output corresponding to the at least one of the heart rate, the respiration rate, the phases of respiration, and the blood pressure on a display;
    selecting a next channel when motion is detected by the present channel, wherein the next channel and the present channel are channels of a same accelerometer in the sensor module; and
    during reconstruction, converting the BCG signals using a pre-defined frequency transfer function between the BCG signals and photoplethysmogram (PPG) signals, wherein reconstructing at least a portion of the decomposed signals into reconstructed signals comprises using time domain smoothing based on one or both of moving averages and the maximum modulus principle.

8. The non-transitory machine-readable medium of claim 7, wherein the BCG signals are decomposed by a function corresponding to one or more of a wavelet, a Hilbert transform, one or more finite impulse response (FIR)/infinite impulse response (IIR) filters with respective cut-off frequencies and stop bands, a time-domain based moving average, and multi-order derivatives.

9. The non-transitory machine-readable medium of claim 7, wherein reconstructing the at least portion of the decomposed signals into reconstructed signals is performed using statistical averaging.

10. The non-transitory machine-readable medium of claim 7, wherein the heart rate is determined based on Cepstrum analysis of at least one of the BCG signals and the reconstructed signals.

11. The non-transitory machine-readable medium of claim 7, wherein channel evaluation criteria for selecting the next channel is based on at least one of a respiration rate estimation confidence indicator determined by peaks in a very low frequency (VLF) band of the channel and a heart rate estimation confidence indicator determined by peaks in a spectrum of the reconstructed signals.

12. The non-transitory machine-readable medium of claim 7, wherein the probability distribution is determined based on an energy contained in each of the decomposed signals.

13. A method for measuring biological signals of a user, comprising:
  acquiring ballistocardiogram (BCG) signals of the user via a present channel, wherein the present channel is at least one channel of a sensor module;
  decomposing the BCG signals into decomposed signals;
  reconstructing at least a portion of the decomposed signals into reconstructed signals using a probability distribution of the decomposed signals;
  processing the reconstructed signals to at least one of a heart rate, a respiration rate, phases of respiration, and a blood pressure;
  displaying at least one output corresponding to the at least one of the heart rate, the respiration rate, the phases of respiration, and the blood pressure on a display;
  selecting a next channel when motion is detected by the present channel, wherein the next channel and the present channel are channels of a same accelerometer in the sensor module; and
  during reconstruction, converting the BCG signals using a pre-defined frequency transfer function between the BCG signals and photoplethysmogram (PPG) signals,
  wherein reconstructing at least a portion of the decomposed signals into reconstructed signals comprises using time domain smoothing based on one or both of moving averages and the maximum modulus principle.

14. The method of claim 13, wherein the probability distribution is determined based on an energy contained in each of the decomposed signals.

15. The method of claim 13, wherein channel evaluation criteria for selecting the next channel is based on at least one of a respiration rate estimation confidence indicator determined by peaks in a very low frequency (VLF) band of the channel and a heart rate estimation confidence indicator determined by peaks in a spectrum of the reconstructed signals.

16. The method of claim 13, wherein the BCG signals are decomposed by a function corresponding to one or more of a wavelet, a Hilbert transform, one or more finite impulse response (FIR)/infinite impulse response (IIR) filters with respective cut-off frequencies and stop bands, a time-domain based moving average, and multi-order derivatives.

17. The method of claim 13, wherein reconstructing the at least portion of the decomposed signals into reconstructed signals is performed using statistical averaging.

18. The method of claim 13, wherein the heart rate is determined based on Cepstrum analysis of at least one of the BCG signals and the reconstructed signals.

* * * * *